US 6,611,326 B1

(12) United States Patent
Yakovlev et al.

(10) Patent No.: US 6,611,326 B1
(45) Date of Patent: Aug. 26, 2003

(54) SYSTEM AND APPARATUS FOR EVALUATING THE EFFECTIVENESS OF WAFER DRYING OPERATIONS

(75) Inventors: Vladislav Yakovlev, Milwaukee, WI (US); Katrina Mikhaylichenko, San Jose, CA (US); Mike Ravkin, Sunnyvale, CA (US); John M. de Larios, Palo Alto, CA (US)

(73) Assignee: Lam Research Corporation, Fremont, CA (US)

( * ) Notice: Subject to any disclaimer, the term of this patent is extended or adjusted under 35 U.S.C. 154(b) by 12 days.

(21) Appl. No.: 09/752,697

(22) Filed: Dec. 27, 2000

(51) Int. Cl.[7] .............................................. G01N 21/00
(52) U.S. Cl. .................................... 356/237.2; 356/394
(58) Field of Search ...................... 356/237.1–237.6, 356/600, 630, 614, 73, 394; 250/559.3, 563, 571–572, 458.1, 459.1, 461.1, 548

(56) References Cited

U.S. PATENT DOCUMENTS

| | | | | |
|---|---|---|---|---|
| 4,556,903 A | * | 12/1985 | Blitchington et al. .... | 356/237.2 |
| 4,744,663 A | * | 5/1988 | Hamashima et al. ..... | 356/237.1 |
| 4,769,551 A | * | 9/1988 | Hamashima et al. ........ | 250/548 |
| 4,871,257 A | * | 10/1989 | Suzuki et al. ............ | 356/237.1 |
| 5,216,479 A | * | 6/1993 | Dotan et al. .................... | 356/73 |
| 5,264,912 A | * | 11/1993 | Vaught et al. ........... | 356/237.1 |
| 5,739,902 A | * | 4/1998 | Gjelsnes et al. ............... | 356/73 |
| 5,963,314 A | * | 10/1999 | Worster et al. .......... | 356/237.2 |
| 6,141,096 A | * | 10/2000 | Stern et al. .............. | 250/458.1 |

\* cited by examiner

Primary Examiner—Frank G. Font
Assistant Examiner—Sang H. Nguyen
(74) Attorney, Agent, or Firm—Martine & Penilla, LLP

(57) ABSTRACT

Systems and apparatus for evaluating the effectiveness of wafer drying techniques are provided. The systems and apparatus include a laser or any other source configured to apply light radiation to the surface of a substrate that has been rinsed with a solution containing an analytically detectable compound prior to a drying process. Any residue of the analytically detectable compound is excited by the source, and the resulting energy is imaged with a confocal microscope or similar device to identify regions of the surface of the substrate of ineffective drying.

28 Claims, 7 Drawing Sheets

SYSTEM AND APPARATUS FOR EVALUATING THE EFFECTIVENESS OF WAFER DRYING OPERATIONS

CROSS REFERENCE TO RELATED APPLICATION

This application is related to U.S. patent application Ser. No. 09/752,609, filed on the same date as the instant application, entitled "METHODS FOR EVALUATING ADVANCED WAFER DRYING TECHNIQUES," and assigned to the same assignee as the instant application. This cross referenced application is hereby incorporated by reference.

BACKGROUND OF THE INVENTION

1. Field of the Invention

The present invention relates generally to wet cleaning of substrates during semiconductor wafer fabrication, and more particularly, to techniques, systems and apparatus for evaluating the effectiveness of techniques used to dry substrates following a wet clean procedure.

2. Description of the Related Art

In the fabrication of semiconductor devices, there is a need to perform wet cleaning of substrates at various stages of the fabrication process. Typically, integrated circuit devices are in the form of multi-level structures. At the substrate level, transistor devices having diffusion regions are formed over and into silicon substrates. In subsequent levels, interconnect metallization lines are patterned and electrically connected to the transistor devices to define the desired functional device. As is well known, patterned conductive layers are insulated from other conductive layers by dielectric materials, such as silicon dioxide. At each metallization level there is a need to planarize metal or associated dielectric material. Without planarization, fabrication of additional metallization layers becomes substantially more difficult due to the higher variations in the surface topography. In some applications, metallization line patterns are formed in the dielectric material, and then metal CMP operations are performed to remove excess metallization.

Following each CMP operation, a wet clean of the substrate is performed. The wet clean is designed to wash away any by-products of the fabrication process, remove contaminants, and to achieve and maintain the necessary degree of cleanliness essential to proceed to a subsequent fabrication operation. As transistor device structures become smaller and more complex, the precision required to achieve and maintain structure definition demands exacting standards of cleanliness be maintained in all process operations. If a wet clean is incomplete or ineffective, or if a post-wet clean drying is incomplete or ineffective, then unacceptable residue or contaminants are introduced into the processing environment.

Rinsing and drying techniques, methods, and apparatus are plentiful and known in the art, and incorporate such operations as rinsing and scrubbing, immersion, and the application of thermal, mechanical, chemical, electrical, or sonic energy and the like to remove or displace water and dry the substrate. While some scrub and rinse operations may employ acids or bases for vigorous interaction with fabrication by-products, deionized water (DIW) is commonly used to perform a final rinse before the desired drying technique is performed.

One common drying technique is known as spin, rinse and dry (SRD). SRD uses mechanical, centrifugal, energy to rid the substrate of water by spinning the substrate until dry. FIG. 1 shows a typical prior art SRD process and apparatus 10. An SRD apparatus 10 typically includes a substrate mounting plate 18 within a bowl 12 and mounted on a shaft 20 that is configured to rotate and thus spin the substrate 14. The substrate 14 is attached to the substrate mounting plate 18 with mounting pins 16 configured to maintain the substrate 14 in a horizontal orientation, firmly affixed to the substrate mounting plate 18 so that rapid rotation of the substrate mounting plate 18 spins the substrate 14 and forces the water from the substrate 18. DIW 26 is typically dispensed from a nozzle 24 which is positioned over the substrate 14 and connected to a DIW supply 22.

The SRD process essentially includes applying DIW or rinsing 28, and spinning the substrate dry 30. In some configurations, the substrate 14 is rinsed 28 while spinning to ensure thorough rinsing 28, and then spun to dry 30. The spinning of the substrate 14 uses centrifugal energy to force water from the substrate 14 surface, and can be enhanced with the introduction of an inert gas such as Nitrogen or an inert gas vapor to displace any water that is not completely removed by spinning. Additional variations include heating the DIW, heating the SRD environment, heating the inert gas, and the like.

Another common drying technique is known as a Marangoni technique. Marangoni drying (not shown) typically includes using a chemical drying fluid or solvent such as isopropyl alcohol (IPA) to introduce favorable surface tension gradients facilitating removal of water from the surface of a substrate. Variations of the Marangoni technique also include the introduction of an inert gas such as Nitrogen as a carrier gas for IPA vapor delivery.

Additionally, another known drying technique involves the replacement of DIW with another volatile compound.

Whichever method or combination of methods is employed to dry a substrate, effective drying is essential to continued fabrication. As is known, contaminates can damage or destroy features that are formed in single dies, groups of dies, or entire wafers.

Any water remaining on the substrate after the drying process evaporates. Water allowed to evaporate introduces contaminants as evidenced by the water marks or stains caused by residual solids from evaporated water. It is therefore desirable to evaluate drying techniques used, recognizing that the techniques are more or less effective depending on such factors as the type of substrate being processed, fabrication materials, processing environment, and the like. Common methods of evaluating the effectiveness of selected drying techniques include visual inspection, electrical analysis and mass analysis.

Visual inspection of substrates is generally effective for blanket film substrates as the surface of the substrate is smooth and easily inspected for remaining water marks. Patterned substrates, however, are difficult to inspect visually as water can be trapped in patterned features and not visible. Visual inspection is therefore ineffective for drying technique evaluation of patterned substrates.

Electrical analysis can be effective for specially prepared test structures after subjecting such structures to an electrical test such as TVS and the like. Such electrical analysis, however, is costly.

Mass analysis is a comparative evaluation of wet and dry substrates. Typically, mass analysis includes an initial drying operation followed by weighing the substrate and then, after some time, re-weighing the substrate to determine if a change in mass has or has not occurred. Although mass analysis is not subject to the same limitations presented by visual inspection and electrical analysis in the evaluation of patterned substrates, mass analysis is cumbersome, time consuming, and far less accurate than other methods.

What is needed is a method to evaluate advanced drying techniques used in the fabrication of semiconductor substrates. The method should include a way to accurately and precisely analyze a substrate that has been dried for any trace amount of residual contamination, and to use the results of the analysis to select, modify, or adjust the drying technique to ensure complete substrate drying in a contaminate-free environment.

SUMMARY OF THE INVENTION

Broadly speaking, the present invention fills these needs by providing a system and apparatus for evaluating drying techniques. The system and apparatus includes applying a compound to a final rinse after a wet clean of a substrate, drying the wafer in accordance with the selected drying technique, and then using a confocal microscope configured to analyze any residual compound on the substrate after the drying method is completed. The present invention can be implemented in numerous ways, including as a process, an apparatus, a system, a device, or a method. Exemplary embodiments of the present invention are described below.

In accordance with one aspect of the invention, an apparatus for measuring the effectiveness of a wafer drying operation is provided. The apparatus includes a laser and a focusing lens to direct laser energy onto a patterned surface of a wafer. A dichroic mirror is provided to direct fluorescent energy emanating from the surface of the wafer. The apparatus further includes a first photomultiplier for capturing an image of the detected fluorescent energy, a partial reflector for directing reflected laser energy from the surface of the wafer, and a second photomultiplier for capturing an image of the reflected laser energy received from the partial reflector. The apparatus then uses the image of the detected fluorescent energy and the reflected laser energy to produce a composite image for evaluating the effectiveness of the wafer drying operation.

In accordance with another aspect of the invention, a system for determining wafer drying effectiveness is provided. The system includes an argon laser to apply laser energy, and a focusing lens to direct the laser energy onto a patterned surface of a wafer. The system further provides a confocal aperture that receives the laser energy from the focusing lens, and a microscope objective that directs the laser energy onto the patterned surface of the wafer. The system next provides a dichroic mirror that directs fluorescent energy received from the surface of the wafer to a first photomultiplier. A partial reflector directs reflected laser energy from the surface of the wafer to a second photomultiplier, and the fluorescent energy and the laser energy are used to evaluate the effectiveness of the wafer drying operation.

In accordance with yet another aspect, an apparatus for quantifying the effectiveness of a wafer drying process is provided. The apparatus includes a laser configured to apply laser energy at a wavelength of about 488 nm, and a focusing lens that directs the laser energy onto a patterned surface of a wafer. The apparatus further provides a dichroic mirror that directs fluorescent energy of a wavelength between about 550 nm and about 650 nm emanating from the surface of the wafer to a first photomultiplier that captures an image of the detected fluorescent energy. The apparatus further includes a partial reflector that directs reflected laser energy of a wavelength of about 488 nm from the surface of the wafer to a second photomultiplier that captures an image of the reflected laser energy received from the partial reflector. The apparatus the uses the image of the detected fluorescent energy and the reflected laser energy to produce a composite image which is used to evaluate the effectiveness of the wafer drying operation.

In yet another embodiment, an apparatus is provided. The apparatus includes an argon laser to apply laser energy and a focusing lens that directs the laser energy onto a patterned surface of a wafer. The apparatus further provides a dichroic mirror to direct fluorescent energy emanating from the surface of the wafer at a first photomultiplier. The first photomultiplier captures an image of the detected fluorescent energy. A partial reflector directs reflected laser energy from the surface of the wafer at a second photomultiplier which captures an image of the reflected laser energy received from the partial reflector. The apparatus then uses the image of the detected fluorescent energy and the reflected laser energy to produce a composite image to evaluate the effectiveness of the wafer drying operation.

In still a further embodiment, an apparatus is provided. The apparatus includes an argon laser that applies laser energy at a wavelength of about 488 nm, and a focusing lens that directs the laser energy onto a patterned surface of a wafer. The apparatus further provides a dichroic mirror that directs fluorescent energy of wavelengths between about 550 nm and about 650 nm emanating from the surface of the wafer at a first photomultiplier which captures an image of the detected fluorescent energy. A partial reflector directs reflected laser energy of wavelengths of about 488 nm from the surface of the wafer at a second photomultiplier which captures an image of the reflected laser energy received from the partial reflector. The image of the detected fluorescent energy and the reflected laser energy is used to produce a composite image for evaluating the effectiveness of the wafer drying operation.

The advantages of the present invention are numerous. One notable benefit and advantage of the invention is the apparatus provide non-biased, quantitative comparison of different drying techniques on patterned wafers. The most commonly utilized prior art of wafer inspection following wet cleans provides no quantitative evaluation, and suffers significant shortcomings as previously detailed. The present invention can be implemented for a plurality of drying techniques, and provides usable, measurable data to evaluate the effectiveness of the selected technique for specific structures, geometries, complexities, and the like.

Another benefit is the cost effectiveness of the present invention. The apparatus are not complicated, and do not require implementation with production, device wafers, but can be used in the R&D stage of production, and with test pattern wafers. This further allows effective evaluation of drying technologies at the stage of concept and feasibility studies, and thus reduces the associated cost of new cleaning tool development.

An additional benefit is that the present invention is an efficient and simple apparatus. Implementation is easily and efficiently incorporated into existing infrastructure, and vastly increases the efficiency of development and production.

Other advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings, wherein like reference numerals designate like structural elements.

DETAILED DESCRIPTION OF EXEMPLARY EMBODIMENTS

An invention for an apparatus and system to evaluate the effectiveness of drying techniques used following a substrate wet clean during semiconductor wafer fabrication is disclosed. In preferred embodiments, the apparatus and system includes rinsing a substrate with a solution of deionized water and a water soluble fluorescent dye, drying the substrate, and then determining the presence of any remaining dye molecules on the surface of the substrate indicating an incomplete or ineffective drying technique. The apparatus and system includes a confocal microscope configured with filters and photomultipliers to detect and assimilate the presence of dye molecules. In the following description, numerous specific details are set forth in order to provide a thorough understanding of the present invention. It will be understood, however, to one skilled in the art, that the present invention may be practiced without some or all of these specific details. In other instances, well known process operations have not been described in detail in order not to unnecessarily obscure the present invention.

Figure 1:
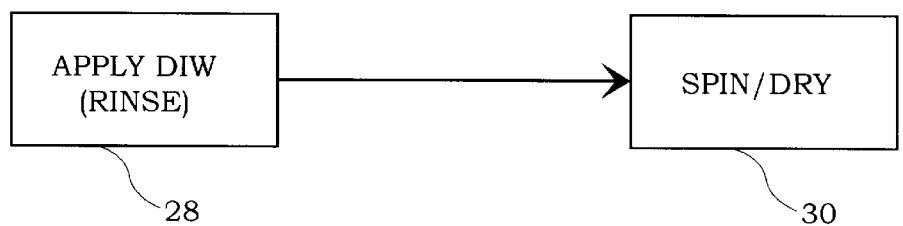
FIG. 1 shows a typical prior art SRD process and apparatus.
Figure 1:
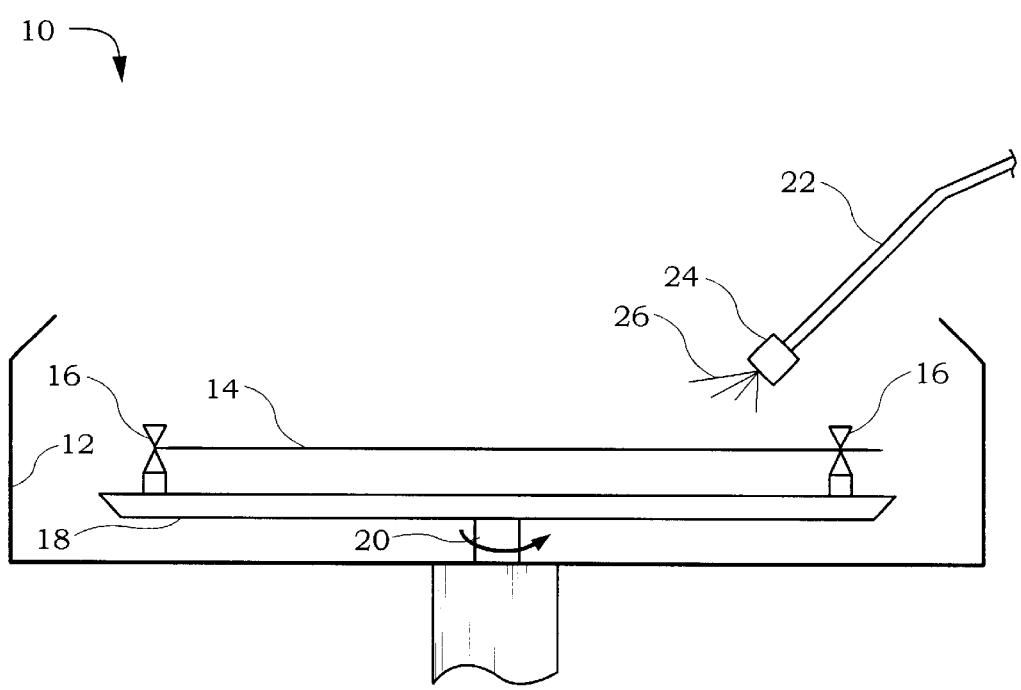
Figure 2A:
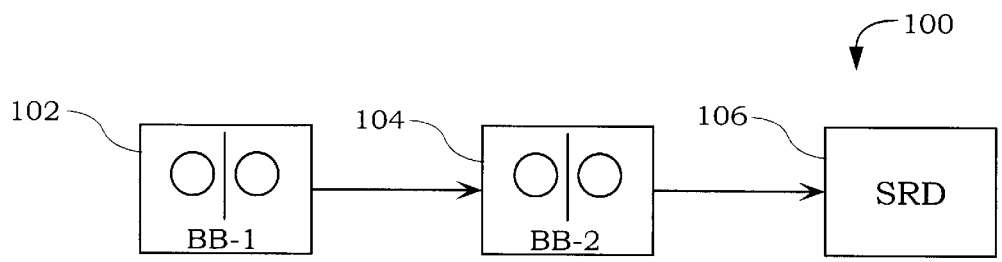
FIG. 2A shows a process flow diagram for a typical wet clean procedure in accordance with one embodiment of the present invention.

FIG. 2A shows a process flow diagram 100 for a typical wet clean procedure in accordance with one embodiment of the present invention. A substrate to be processed through a wet clean is processed through brush box 1 (BB-1) 102, followed by brush box 2 (BB-2) 104, and then rinsed and dried in a spin-rinse-dry (SRD) apparatus 106. In some cases, only one brush box need be used. One alternative to the SRD 106 drying operation is a Marangoni drying technique which is known in the field of semiconductor wafer fabrication. Another alternative to the SRD 106 drying operation is an HFE dryer, which is also a known technique and apparatus. The process flow diagram 100 is configured to clean any by-products of fabrication processes, remove any contamination from the wafer, and dry the wafer in preparation for subsequent fabrication operations. One embodiment of the present invention is incorporated into the SRD 106 apparatus and process, as described below in reference to FIG. 2B.

Figure 2B:
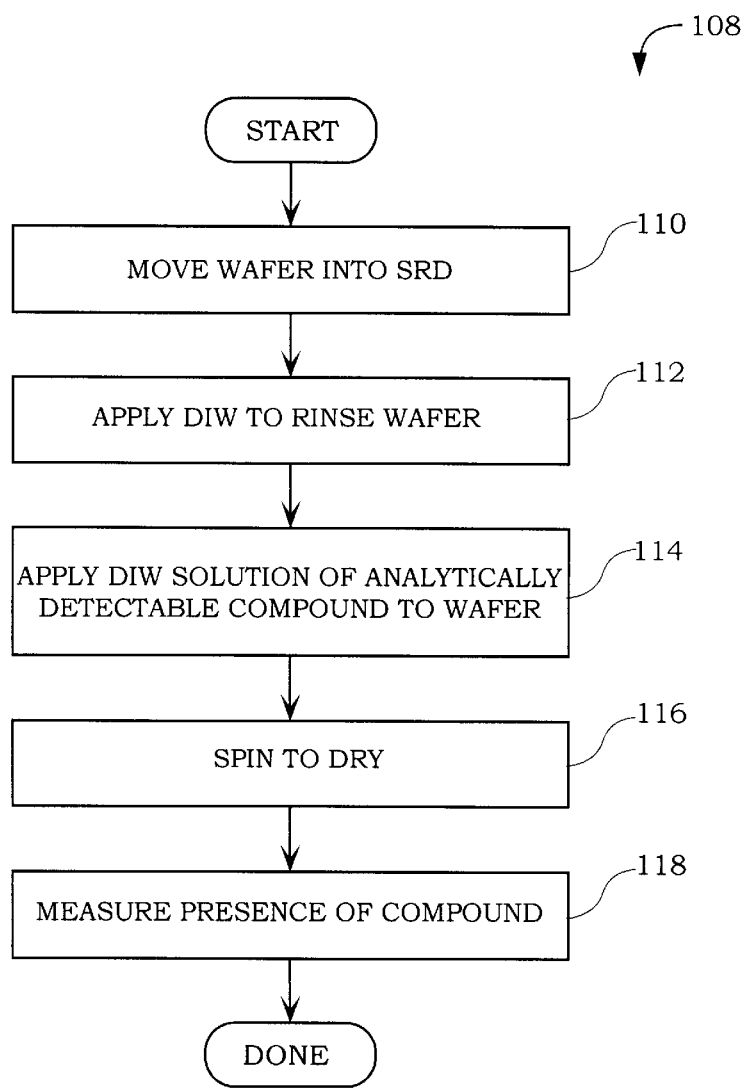
FIG. 2B is a high-level flow chart illustrating the method operations of evaluating drying techniques in accordance with an embodiment of the present invention.

FIG. 2B is a high-level flow chart 108 illustrating the method operations for evaluating drying techniques in accordance with an embodiment of the present invention. The method operations identified in the high-level flow chart 108 are general, broad category method operations that are developed in greater detail in reference to FIGS. 3A–4C. As described above in reference to FIG. 2A, the method begins at operation 110 in which a wafer is moved into an SRD. Typically, the wafer has been processed through a wet clean, including the operations of scrubbing in a first brush box and a second brush box. In one embodiment, the wet clean process includes a scrubbing of the wafer with deionized water (DIW), ammonium hydroxide, an hydrofluoric acid or some other chemical in BB-1 102 (FIG. 2A), and then a rinsing and scrubbing of the wafer with deionized water in BB-2 104 (FIG. 2A). As the wafer is processed through the wet clean, the wafer is moved into the SRD as identified in operation 110.

The method advances to operation 112 in which DIW is applied to rinse the wafer. Operation 112 represents a typical "final" rinse of a wet clean procedure once the wafer has been inserted into the SRD.

In operation 114, an analytically detectable compound in a solution with DIW is applied to the wafer. As will be described in greater detail below, the compound, in a preferred embodiment, is truly soluble in water. The solution of DIW and the compound is applied over the entire surface of the wafer. Variables such as flow rate, concentration of the compound, and duration of application are discussed in greater detail below.

Once the compound in solution has been applied to the wafer in operation 114, the method advances to operation 116 in which the wafer is spun dry in accordance with known techniques for utilizing an SRD to dry a wafer. In an alternative embodiment, the wafer drying technique is a Marangoni method, and in operation 116 the water would be removed using the assistance of applied isopropyl alcohol (IPA), or immersed or otherwise bathed in IPA or other drying fluid in order to accomplish the drying of the wafer.

The method concludes with operation 118 in which the presence of the compound, or compound residue, is measured on the dried wafer. As will be described in greater detail below, the dried wafer is inspected and analyzed to detect the presence of the compound, and thus the selected drying technique is evaluated for effectiveness, and modified accordingly.

In one embodiment of the present invention, the compound is selected in accordance with the analytical technique employed to inspect and analyze the substrate. The compound should be truly soluble in water, non-volatile, and easily detectable by the analytical technique selected. By way of example, analytical techniques might include spectroscopic or fluorescent detection and analysis, and the like. The compound in such an embodiment might be a laser dye such as Rhodamine 590 which is easily detectable in solution and as a residue after any liquid has evaporated. Other exemplary laser dyes may include Rhodamine 610, Kiton Red 620, Rhodamine 640, Coumarin 450, Coumarin 480, Coumarin 487, LD 489, Coumarin 500, and other such dyes.

Dyes may include any organic or inorganic material producing fluorescence under external excitation.

Therefore, after the selected compound in solution has been applied, and the wafer has been dried in accordance with the selected drying method or technique, if any solution remains on the surface of the substrate or in the patterned features, the remaining solution would evaporate, but a solid residue of the selected compound would remain and would be detectable spectroscopically, fluorescently, or in a similar analytical detection manner.

Figure 3A:
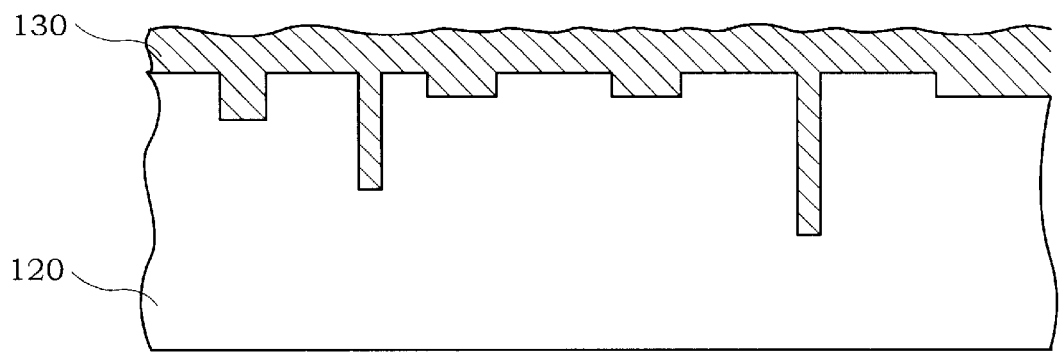
FIG. 3A shows a cross section of a patterned wafer in accordance with one embodiment of the invention.

One embodiment of the present invention provides an optimal method of evaluating the drying technique selected for drying a patterned wafer. The intricate features present in a patterned wafer provide the space and opportunity for water to be trapped during a wet clean, and further, to obscure the trapped water and residue (e.g., once the water has evaporated) from common visual inspection techniques. FIG. 3A shows a cross section of a patterned wafer 120 in accordance with one embodiment of the invention. A compound in solution 130 is applied to the surface of the wafer 120. The surface of the wafer 120 includes a varied topography resulting from the representative features being fabricated. FIG. 3A shows representative features including, for example, shallow trenches, deep trenches, broad trenches, and very narrow trenches. While not all-inclusive of the plurality of features resulting during the fabrication of semiconductor devices, the features shown in FIG. 3A illustrate a surface capable of trapping water within the patterned structures.

The compound in solution 130 is applied to completely cover the surface and fill the features of the patterned wafer 120. Because the compound must be completely distributed over the surface of the wafer where the DIW is and is capable of being distributed, the compound must be truly soluble in water. An alternative embodiment discussed in greater detail below contains particles in suspension, but in the embodiment illustrated in FIG. 3A, the compound is in solution. Any surface covered with DIW is therefore covered with the solution as illustrated in FIG. 3A.

In order to ensure complete coverage of the wafer 120 with the compound in solution 130, at least three variables of the compound in solution 130 are monitored and adjusted as necessary: flow rate, duration of application, and concentration of compound in solution. The flow rate of the compound in solution 130 when it is applied to the wafer 120 is anticipated to range from about 100 ml/min.–1000 ml/min., with a preferred flow rate of about 400 ml/min. Such factors as the size of the wafer, the size and type of patterned features, the rate of rotation of the wafer (in an SRD embodiment), process conditions such as process environment temperature, pressure, and solution viscosity, and the like are considered in determining an optimum flow rate for a specific application. Accordingly, the flow rate ranges will vary depending upon the particular environment parameters.

The duration of the application of the compound in solution 130 to the surface of the wafer 120 (e.g., the length of time the solution is on the surface of the wafer before the drying process is commenced) is anticipated to range between about 1 second and about 5 minutes for most acceptable solutions, between about 10 seconds and about 1 minute for a preferred embodiment using a laser dye solution, with a typical duration of about 20 seconds. The duration of application varies with the above-listed factors, and more particularly with the specific compound in solution selected.

The concentration of the selected solution also varies in accordance with the above listed factors, with a primary consideration being the detection method selected. In a preferred embodiment of the invention, the detection method is a laser spectroscopy, and the compound selected would be a form of laser dye. It is anticipated that the concentration of the selected compound in DIW will range from about $10^{-6}$ grams/liter to about $10^{-2}$ grams/liter, with a preferred concentration of about $10^{-3}$ grams/liter. The concentration, however, may vary significantly with the different types of analytically detectable compounds, and must be optimized accordingly. Other types of analytically detectable compounds include $NaHSO_4$, $CS_2$, Benzene detectable by Raman spectroscopy, CdS, CdSe detectable with luminescence, and the like.

Figure 3B:
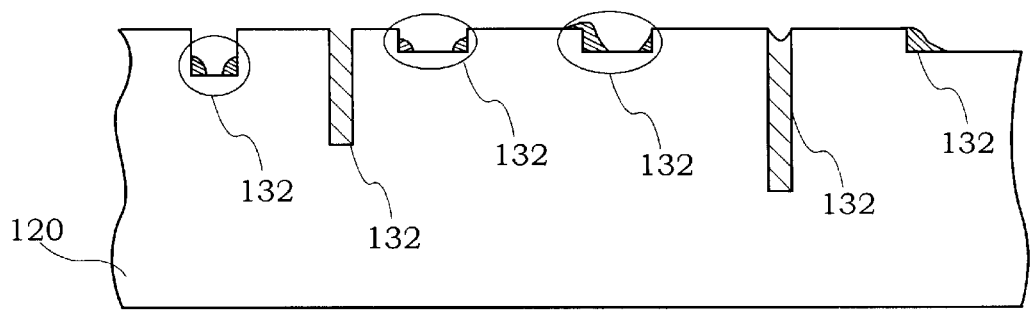
FIG. 3B shows the wafer of FIG. 3A immediately after the drying process in accordance with one embodiment of the invention.

FIG. 3B shows the wafer 120 of FIG. 3A immediately after the drying process in accordance with one embodiment of the invention. By way of example, the drying process may have been an SRD. Some of the compound and DIW in solution 132 remains trapped on the surface of the wafer 120 and inside the patterned features. The amount of remaining compound and DIW in solution 132 has been exaggerated in FIG. 3B to illustrate the various regions in pattern features where the solution 132 can commonly remain trapped. The SRD drying technique involves a mechanical drying process of spinning the wafer as described above, and as illustrated in the embodiment shown in FIG. 3B, the mechanical process alone may not be effective in completely removing the solution from the surface, or drying the surface of a patterned substrate with complex pattern features. In more complex patterns, mechanical spinning may not be effective in thoroughly removing water from the corners or in deep or narrow trenches of the pattern.

Figure 3C:
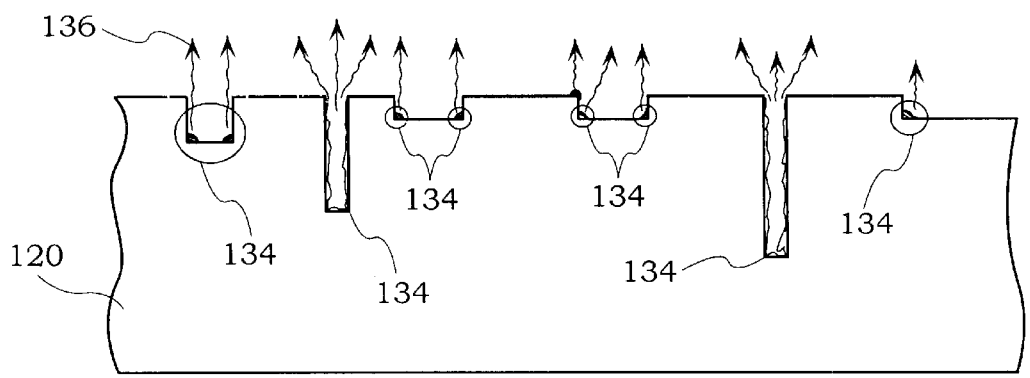
FIG. 3C shows the wafer of FIGS. 3A and 3B after the wafer has been allowed to stand and any remaining solution has evaporated in accordance with one embodiment of the invention.

FIG. 3C shows the wafer 120 of FIGS. 3A and 3B after the wafer has been allowed to stand and any remaining solution 132 (FIG. 3B) has evaporated in accordance with one embodiment of the invention. A solid residue of the compound 134 remains in those features where the remaining solution 132 was trapped. The compound, and its residue 134, is analytically detectable. In FIG. 3C, a signal 136 is shown emanating from the residue 134. In one embodiment, the strength of the signal 136 is directly proportional to the amount of compound residue 134 remaining on the wafer 120 and in the pattern features. The wafer 120 is analyzed to detect any presence of the signal 136, and evaluated to determine the effectiveness of the selected drying technique. The signal 136 might be a fluorescent radiation from the solid residue of a laser dye that can be easily detected, measured, evaluated, and mapped to provide a comprehensive evaluation of the selected drying technique.

In one embodiment of the present invention, the analysis of the wafer is not a comprehensive analysis of each and every square micron of the wafer surface, but a scan of the wafer surface, and a detailed analysis of selected, representative regions of the wafer. As is known, a semiconductor wafer is typically fabricated as a plurality of dies. Each die includes a plurality of specific, semiconductor structures. Each specific semiconductor structure contains a plurality of specific patterned features. In the present invention, a few dies are selected for analysis as representative of a plurality of regions of a semiconductor wafer surface. By way of example, a die from near a center region of the wafer, one from near a mid-radius region of the wafer, and a die from near an edge of the wafer might be identified for comprehensive analysis.

Figure 4A:
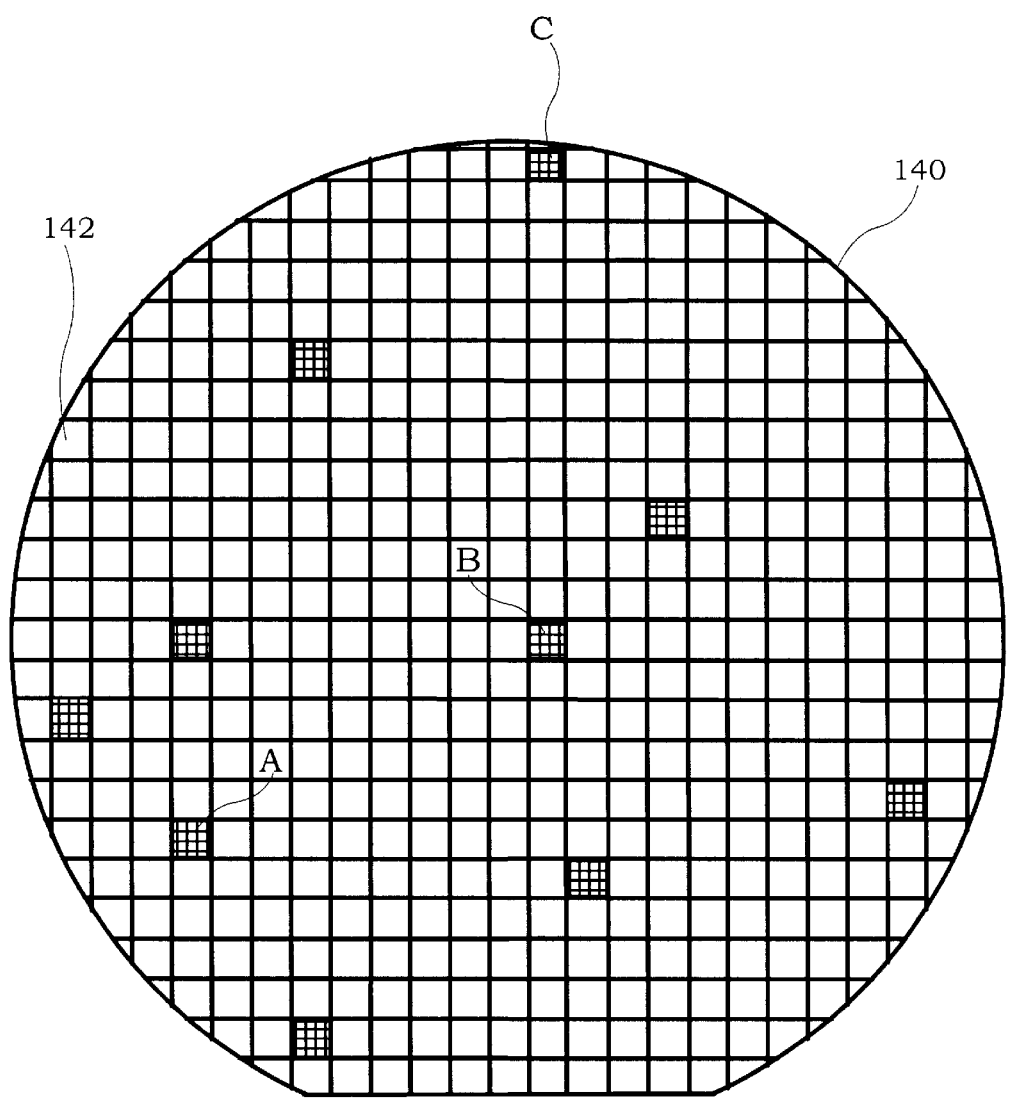
FIG. 4A illustrates a patterned semiconductor wafer.

FIG. 4A illustrates a patterned semiconductor wafer 140. The patterned semiconductor wafer 140 may be at any stage of the fabrication process. The surface of the wafer 140 is divided into a plurality of small squares representing the dies 142 on the surface of the wafer 140. As described above, each of the dies 142 includes a plurality of semiconductor structures that are fabricated, or are in the process of being fabricated, on the wafer 140. In accordance with an embodiment of the present invention, representative dies "A", "B", and "C" are identified to be analyzed to evaluate a selected drying technique following a wet clean.

Figure 4B:
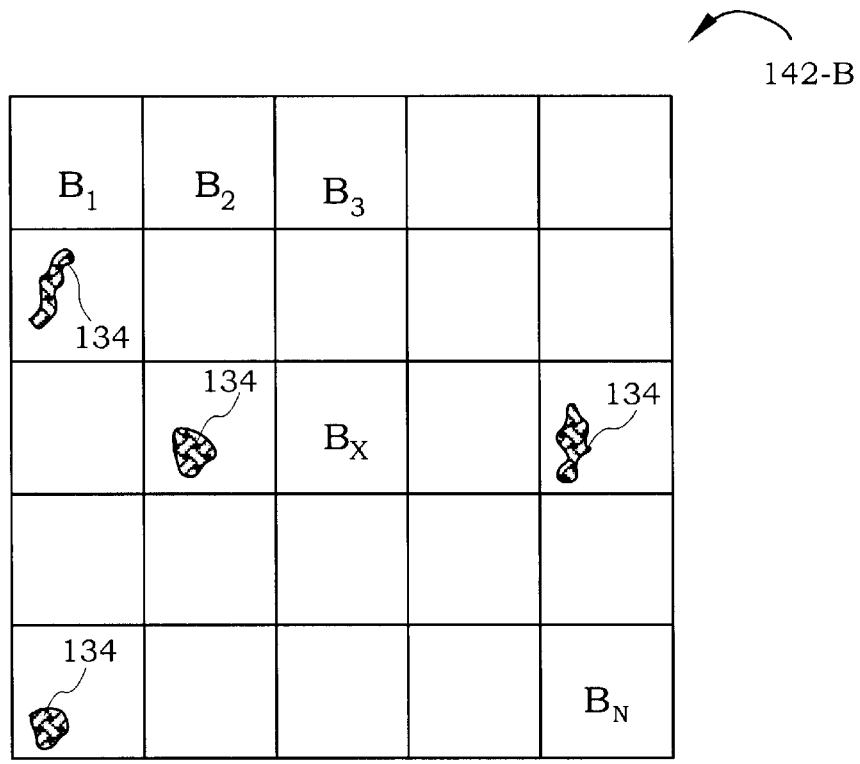
FIG. 4B shows a selected die from the patterned wafer of FIG. 4A in accordance with one embodiment of the present invention.

Looking closer at selected die "B", FIG. 4B shows the selected die 142-B from the patterned wafer of FIG. 4A in accordance with one embodiment of the present invention. As described above, each die 142 includes a plurality of semiconductor structures. The plurality of semiconductor structures can be grouped, by way of example, into like structures, or into combinations of structures performing a common function. A selected die 142-B can be further subdivided into a plurality of regions as illustrated in FIG. 4B and designated $B_1$, $B_2$, $B_3$, ..., $B_X$, ..., $B_N$. Some of the plurality of regions contain complex and densely fabricated semiconductor structures, and some of the plurality of regions contain less complex and less densely fabricated semiconductor structures. In one embodiment of the invention, a meaningful evaluation of a drying technique would include an analysis of all ranges of complexity and density of structure and feature fabricated on a semiconductor wafer 142 (FIG. 4A). Compound residue 134 is shown on selected die 142-B.

Figure 4C:
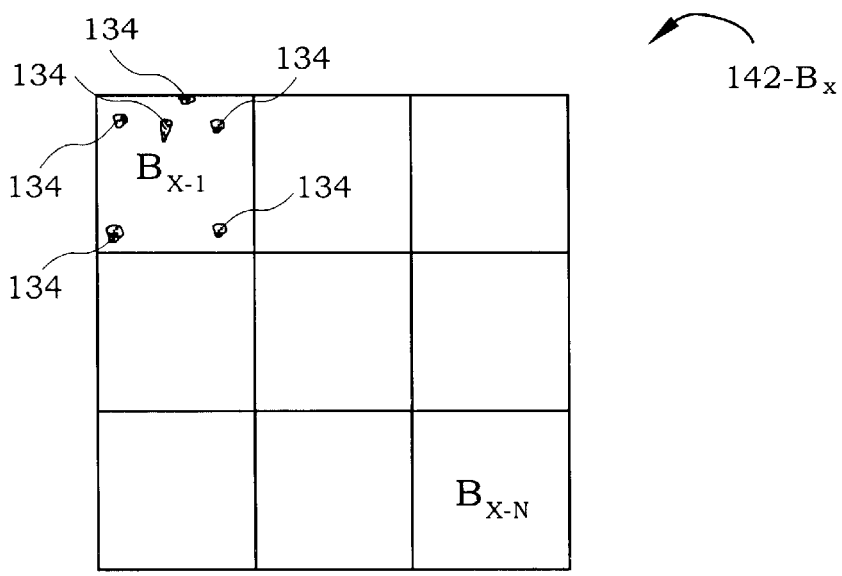
FIG. 4C shows a further subdivision of the selected die shown in FIG. 4B.

FIG. 4C shows a further subdivision 142-$B_X$ of the selected die 142-B shown in FIG. 4B. Depending on the complexity and density of the semiconductor structures fabricated in a selected die 142-B, a plurality of subdivisions 142-$B_X$ may be identified in order to analyze individual features, combinations of features, and entire structures. By way of example, specific geometries of structures or features, or specific locations on a die 142 (FIG. 4A), 142-B (FIG. 4B), may exhibit a tendency to retain solution and resulting compound residue 134. Semiconductor wafers are typically fabricated in large volumes, and particular drying techniques can thereby be identified as most effective for specific wafer fabrication patterns.

The presence of compound residue 134 reveals that water was not completely removed, mechanically, during the drying process. In optimizing the selected drying technique, a number of variables can be adjusted and modified. Examples of variables include the speed of drying, the presence and/or volume of nitrogen blow, whether or not nitrogen blow is heated, the flow of IPA in Marangoni systems, and the like. The method of the present invention, in one embodiment, can be used to optimize a selected drying technique, and such variables can be modified, combined, or otherwise adjusted to achieve the optimum drying technique for specific wafer materials and patterns.

In one embodiment of the present invention, an apparatus and system are implemented to analyze and evaluate selected drying techniques in accordance with the above description. The apparatus and system include the use of a fluorescent dye as the analytical compound. Examples of fluorescent dyes include Rhodamine 590, Rhodamine 610, and Kiton Red 620 which are available from Exciton, Inc., of Dayton, Ohio.

A solution of fluorescent dye and DIW is used to rinse a substrate prior to drying as described above. The substrate is then dried using a desired technique, and after a period of time, any solution remaining on the substrate after the drying process evaporates leaving molecules (e.g., residues) of the fluorescent dye behind. The molecules of fluorescent dye are excited with a laser, and the resulting fluorescence is measured with a confocal microscope.

Figure 5:
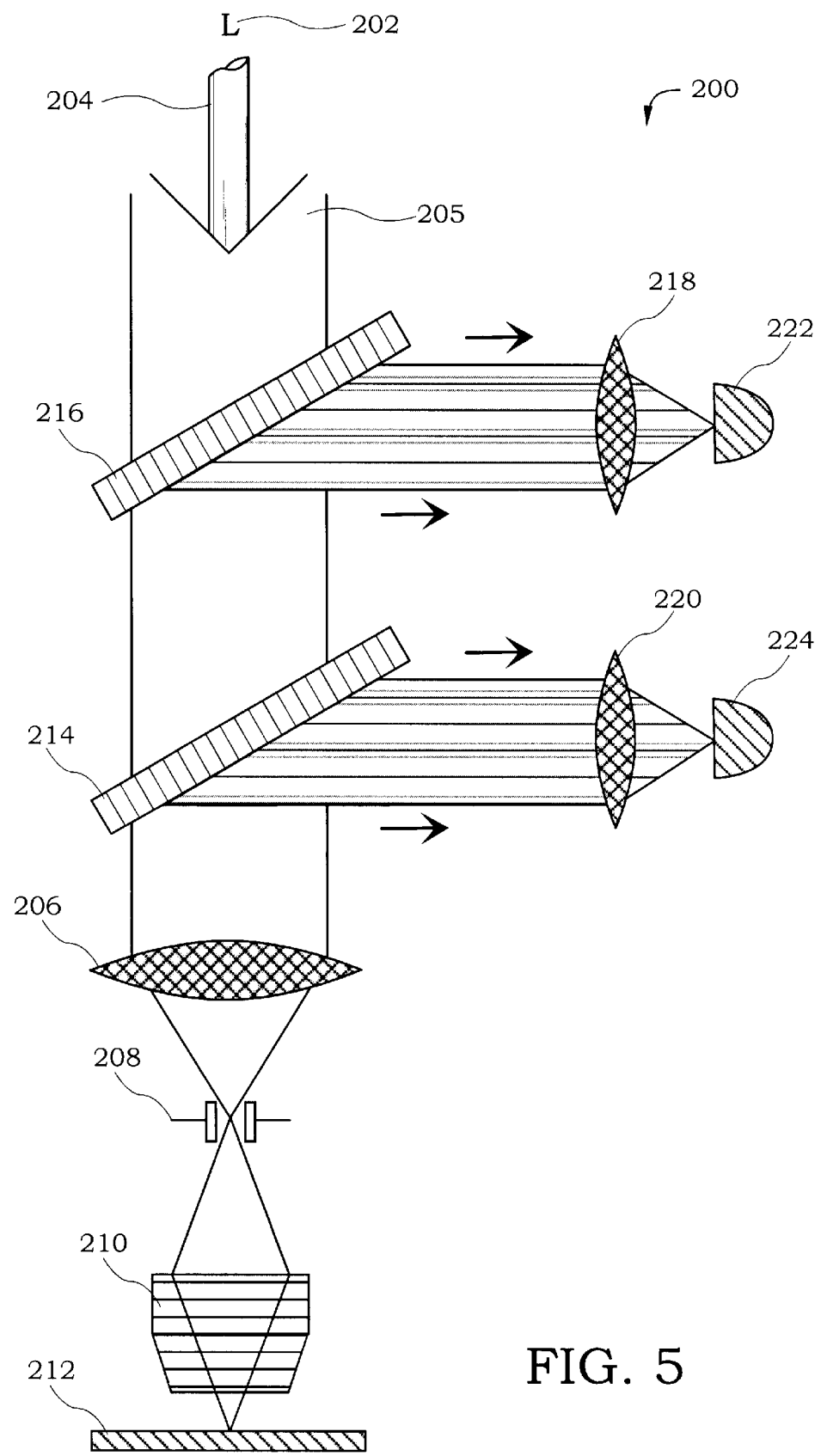
FIG. 5 is a confocal microscope configured to measure fluorescence on a substrate in accordance with one embodiment of the present invention.

FIG. 5 is a confocal microscope 200 configured to measure fluorescence on a substrate in accordance with one embodiment of the present invention. A laser source 202 is directed 204 at a desired point on a substrate 212 after the substrate has been dried and any solution remaining on the substrate has evaporated. In one embodiment, the laser source is an Ar+-laser, projecting a 488 nm line wavelength, at approximately 2 mW. The laser beam 205 is focussed through a focusing lens 206, and through a confocal aperture 208. In one embodiment, the confocal aperture is set to about 50 microns. The laser beam 205 then travels through the microscope objective 210 and is directed at a selected location on the surface of the substrate 212. In one embodiment, the objective has an N.A. of 0.4.

Any remaining fluorescent dye molecules remaining on the surface of the substrate 212 are excited by the laser beam 205, producing fluorescence which is imaged by the present invention. The reflected laser and any fluorescence follows a return path of the laser beam 205. A dichroic mirror 214 is configured to select the appropriate wavelength of fluorescence and directs the fluorescence through focusing lens 220 to photomultiplier 224 which contains an interference filter for the appropriate wave length of the fluorescence so that only the fluorescence is captured. In one embodiment, the dichroic mirror 214 is configured to be used with the appropriate fluorescent dye, Rhodamine 590 for example, so that the 488 nm wavelength of the laser beam 205 passes through the dichroic mirror 214, but the approximately 550–650 nm wavelength of the fluorescence is reflected and sent through focusing lens 220 to photomultiplier 224. The photomultiplier 224 in this embodiment would include an interference filter for the approximately 550–650 nm wavelength so that only the fluorescence is captured.

The reflected laser beam 205, being of a different wavelength than the fluorescence, continues to partial reflector 216 which is configured for the appropriate wavelength of the laser beam 205. The reflected laser beam is directed through focusing lens 218 and to photomultiplier 222 which is configured with an appropriate filter for the laser wave length. In one embodiment, the laser beam 205 has a wave length of 488 nm. The partial reflector 216 is configured to reflect wavelength 488 nm, directing it through the focusing lens 218 and to photomultiplier 222 which is configured with an interference filter for 488 nm so that only the 488 nm reflected laser beam is captured.

The confocal microscope 200 of the present invention thus processes two images using the captured wavelengths in photomultipliers 222 and 224. Photomultiplier 222 produces an image of the substrate 212 surface. Photomultiplier 224 produces an image of fluorescence from the substrate 212. In one embodiment, the images are combined to determine those points on the substrate 212 where the selected drying technique failed to remove all of the solution, leaving fluorescent dye on the surface or in the features of a patterned wafer. Multiple samplings of substrate images can be evaluated to modify and optimize the drying technique in accordance with structures being fabricated. In one embodiment, the substrate is positioned on a translational stage. The translational stage is configured for movement in the X, Y, and Z axes to allow for scanning across all points of the surface of the substrate, as well as focusing at the surface or at the depth of the shallow trench structures, or any desired depth of the patterned substrate.

A preferred embodiment of the present invention is implemented in the research and development (R&D) stage of semiconductor fabrication. Typically, large volumes of identical semiconductor structures are mass produced for the most efficient use of tools, materials, and other resources. In one embodiment of the present invention, the drying technique to be used for a particular production wafer is determined and evaluated in the ramp up to production. With data developed during the R&D of the particular semiconductor structure and production wafer, the implementation of the drying techniques employed during various stages of fabrication is readily determinable, and subject to verification to maximize efficiency of production.

Test pattern wafers are commonly used in R&D, and provide a comprehensive evaluation of processes for a plurality of structures and features typically fabricated on a substrate. As described above in reference to FIGS. 4A–4C, semiconductor devices are typically fabricated in dies with a plurality of dies patterned on a substrate. Test pattern wafers include a plurality of dies and are configured to present similar structures and configurations for use in, for example, R&D or characterization of semiconductor fabrication tools. In one embodiment of the present invention, a test pattern wafer is used to implement the method, system and apparatus described above.

Figure 6A:
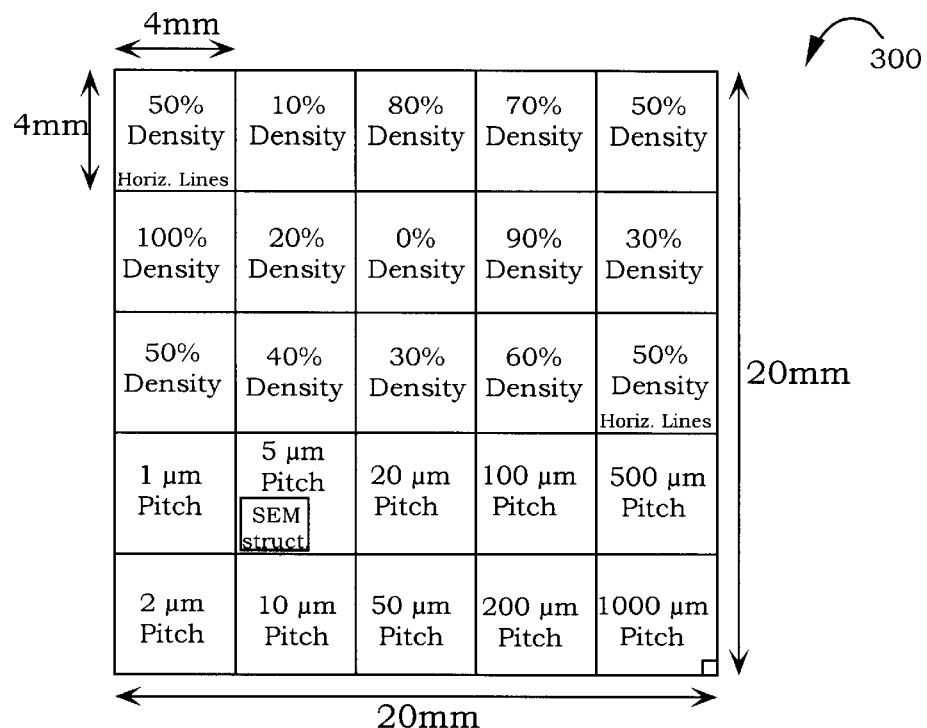
FIG. 6A shows a typical die of a test pattern wafer.

FIG. 6A shows a typical die 300 of a test pattern wafer. A single die 300 is configured to present a comprehensive area of varying densities, complexities and geometries of the features and structures of semiconductor devices. The die 300 in FIG. 6A presents a 5×5 region of varying densities, pitches, and geometries. As is known, pattern density is defined as the active width divided by the sum of the trench width and the active width. Further, pitch is defined as the sum of the trench width and the active width. By varying both pattern density and pitch, the test pattern wafer 300 simulates a broad spectrum of structure types and complexities. The test pattern wafer 300 also varies pattern geometry in selected regions.

Figure 6B:
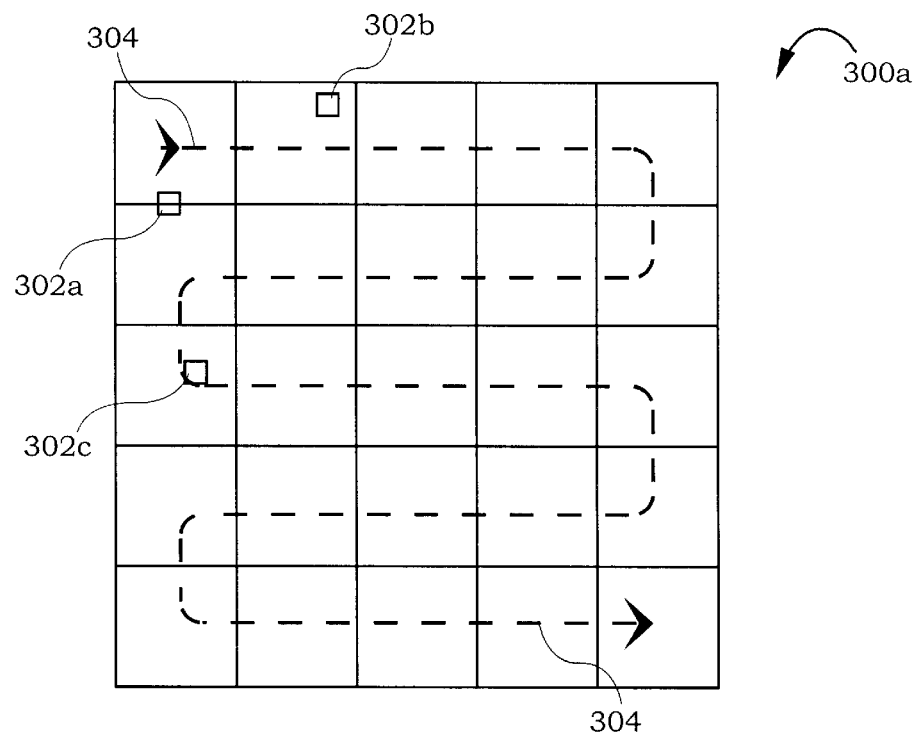
FIG. 6B illustrates laser scan pattern options in accordance with embodiments of the invention.

FIG. 6B illustrates laser scan pattern options in accordance with embodiments of the invention. A test pattern die 300a is represented as a 5×5 grid to illustrate the plurality of regions contained therein. The variation in regions is shown in FIG. 6A. A confocal microscope 200 as described in FIG. 5 is used to scan and image selected dies 300a to produce an image of the test pattern die 300a and any areas of incomplete or ineffective substrate drying. In one embodiment, the test pattern die 300a is imaged at pre-designated points 302a, 302b, 302c. Such points are selected based on such criteria as the type of drying method being evaluated, the type of semiconductor device that will be fabricated, the features presented in particular regions of the test pattern die 300a, and the like. By way of example, point 302a presents an intersection between pattern densities and geometries, point 302b presents an outer edge of a particular region, and point 302c presents a center of a particular region. Such points can be scanned and evaluated in a pre-designated and specific method, or can be randomly selected points on the test pattern die 300a.

An alternative embodiment of implementing the present invention is to perform a scan of the test pattern die 300a. Such a scan may be a raster scan, or a scan pattern 304 as illustrated in FIG. 6B. The confocal microscope 200 (FIG. 5) can be configured to scan across the test pattern die 300a, positioning the laser beam on the surface of the test pattern die 300a to produce an image showing the distribution of ineffective drying on the surface of the test pattern die 300a. As described above in reference to FIG. 5, the substrate is positioned on a translational stage in one embodiment providing positioning and movement of the substrate in either or each of the X, Y, and Z axes.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. An apparatus for measuring the effectiveness of a wafer drying operation, comprising:

a laser for applying laser energy;

a focusing lens for directing the laser energy onto a patterned surface of a wafer;

a dichroic mirror for directing fluorescent energy emanating from the surface of the wafer;

a first photomultiplier for capturing an image of detected fluorescent energy;

a partial reflector for directing reflected laser energy from the surface of the wafer; and a second photomultiplier for capturing an image of the reflected laser energy received from the partial reflector; the image of the detected fluorescent energy and the reflected laser energy used to produce a composite image used to evaluate the effectiveness of the wafer drying operation, wherein the laser directs laser energy through each of the partial reflector, the dichroic mirror, and the focusing lens before the laser energy is received on the patterned surface of the wafer and the reflected laser energy and the fluorescent energy emanating from the surface of the wafer return through the focusing lens to the dichroic mirror through which the reflected laser energy passes, the reflected laser energy continuing to the partial reflector.

2. An apparatus for measuring the effectiveness of a wafer drying operation as recited in claim 1, wherein the laser is an Argon laser having a wavelength of about 488 nm.

3. An apparatus for measuring the effectiveness of a wafer drying operation as recited in claim 2, wherein the detected fluorescent energy is created by the Argon laser exciting residual molecules of laser dye in the patterned surface of the wafer.

4. An apparatus for measuring the effectiveness of a wafer drying operation as recited in claim 1, wherein the image of the reflected laser energy shows the patterned surface of the wafer.

5. An apparatus for measuring the effectiveness of a wafer drying operation as recited in claim 1, wherein the image of the fluorescent energy shows locations where a selected wafer drying technique did not completely remove a solution from the patterned surface of the wafer.

6. A system for determining wafer drying effectiveness, comprising:

an argon laser for applying laser energy;

a focusing lens for directing the laser energy onto a patterned surface of a wafer;

a confocal aperture for receiving the laser energy from the focusing lens;

a microscope objective for directing the laser energy onto the patterned surface of the wafer;

a dichroic mirror for directing fluorescent energy received from the surface of the wafer;

a first photomultiplier for obtaining the received fluorescent energy;

a partial reflector for directing reflected laser energy from the patterned surface of the wafer; and a second photomultiplier for obtaining the reflected laser energy received from the partial reflector; the obtained fluorescent energy and the obtained laser energy used to evaluate the effectiveness of the wafer drying operation, wherein the argon laser, the focusing lens, the confocal aperture, the microscope objective, the dichroic mirror, the first photomultiplier, the partial reflector and the second photomultiplier are arranged in the system so that laser energy from the argon laser is directed through the partial reflector, through the dichroic mirror, through the focusing lens, through the confocal aperture, and through the microscope objective to be received on the patterned surface of the wafer, and fluorescent energy and reflected laser energy travel from the patterned surface of the wafer through the microscope objective and through the confocal aperture, the reflected laser energy traveling through the dichroic mirror to the partial reflector.

7. A system for determining wafer drying effectiveness as recited in claim 6, wherein the first photomultiplier produces an image of areas of incomplete drying and the second photomultiplier produces an image of the patterned surface of the wafer.

8. A system for determining wafer drying effectiveness as recited in claim 7, further comprising producing a composite image including the patterned surface of the wafer and areas of incomplete drying, and wherein the evaluating the effectiveness of the wafer drying operation includes an analysis of the composite image.

9. A system for determining wafer drying effectiveness as recited in claim 6, wherein the argon laser has a wavelength of about 488 nm.

10. A system for determining wafer drying effectiveness as recited in claim 6, wherein the fluorescent energy has a wavelength of about 550 to about 650 nm.

11. An apparatus for quantifying the effectiveness of a wafer drying process, comprising:

a laser for applying laser energy having a wavelength of about 488 nm;

a focusing lens for directing the laser energy onto a patterned surface of a wafer;

a dichroic mirror for directing fluorescent energy having wavelengths between about 550 nm and about 650 nm emanating from the surface of the wafer;

a first photomultiplier for capturing an image of the detected fluorescent energy;

a partial reflector for directing reflected laser energy having wavelengths of about 488 nm from the patterned surface of the wafer; and a second photomultiplier for capturing an image of the reflected laser energy received from the partial reflector; the image of the detected fluorescent energy and the reflected laser energy used to produce a composite image used to evaluate the effectiveness of the wafer drying operation.

12. An apparatus for quantifying the effectiveness of a wafer drying process as recited in claim 11, further comprising:

a confocal aperture for restricting the laser energy to an opening of about 50 microns;

a confocal microscope objective for directing the laser energy, wherein the confocal microscope objective has an N.A. of about 0.4; and a translational stage for supporting and for positioning the wafer in the X, Y, and Z axes.

13. An apparatus for quantifying the effectiveness of a wafer drying process as recited in claim 12, wherein the fluorescent energy is produced by the laser energy exciting molecules from fluorescent dye on the patterned surface of the wafer.

14. An apparatus for quantifying the effectiveness of a wafer drying process as recited in claim 13, wherein the molecules from fluorescent dye are present on the patterned surface of the wafer in regions of incomplete drying of the wafer by a selected wafer drying operation.

15. An apparatus for quantifying the effectiveness of a wafer drying process as recited in claim 14, wherein the evaluating the effectiveness of the wafer drying operation includes analysis of the regions of incomplete drying of the wafer by the selected wafer drying operation.

16. An apparatus, comprising:

an argon laser for applying laser energy;

a focusing lens for directing the laser energy onto a patterned surface of a wafer;

a dichroic mirror for directing fluorescent energy emanating from the surface of the wafer;

a first photomultiplier for capturing an image of the detected fluorescent energy;

a partial reflector for directing reflected laser energy from the surface of the wafer; and a second photomultiplier for capturing an image of the reflected laser energy received from the partial reflector; the image of the detected fluorescent energy and the reflected laser energy used to produce a composite image used to evaluate the effectiveness of the wafer drying operation.

17. An apparatus as recited in claim 16, further comprising:

a confocal aperture for restricting the laser energy that is directed onto the patterned surface of the wafer, wherein the confocal aperture is set to about 50 microns;

a confocal microscope objective for directing the laser energy, wherein the confocal microscope objective has an N.A. of about 0.4; and a translational stage for supporting and for positioning the wafer in the X, Y, and Z axes.

18. An apparatus as recited in claim 16, wherein the argon laser has a wavelength of about 488 nm and wherein the fluorescent energy has a wavelength of about 550 nm to about 650 nm.

19. An apparatus as recited in claim 16, wherein the dichroic mirror is configured to select the wavelength of the fluorescent energy and direct the selected energy to the first photomultiplier while allowing wavelengths other than the selected wavelength to pass through the dichroic mirror.

20. An apparatus, comprising:

an argon laser for applying laser energy having a wavelength of about 488 nm;

a focusing lens for directing the laser energy onto a patterned surface of a wafer;

a dichroic mirror for directing fluorescent energy having wavelengths between about 550 nm and about 650 nm emanating from the surface of the wafer;

a first photomultiplier for capturing an image of the detected fluorescent energy;

a partial reflector for directing reflected laser energy having wavelengths of about 488 nm from the surface of the wafer; and a second photomultiplier for capturing an image of the reflected laser energy received from the partial reflector; the image of the detected fluorescent energy and the reflected laser energy used to produce a composite image used to evaluate the effectiveness of the wafer drying operation.

21. An apparatus as recited in claim 20, further comprising:

a confocal aperture for restricting the laser energy that is directed onto the patterned surface of the wafer;

a confocal microscope objective for directing the laser energy after the laser energy passes through the confocal aperture; and a translational stage for supporting and for positioning the wafer.

22. An apparatus as recited in claim 21, wherein the first photomultiplier includes an interference filter for the same wavelength as the laser energy directed by the partial reflector, the interference filter being configured to provide that only the laser energy is captured.

23. An apparatus as recited in claim 21, wherein the second photomultiplier includes an interference filter for the same wavelength as the fluorescent energy directed by the dichroic mirror, the interference filter being configured to provide that only the fluorescent energy is captured.

24. An apparatus for measuring the effectiveness of a wafer drying operation, comprising:

a source of light radiation;

a focusing lens for directing the light radiation onto a patterned surface of a wafer;

a dichroic mirror for directing fluorescent energy emanating from the surface of the wafer;

a first photomultiplier for capturing an image of detected fluorescent energy;

a partial reflector for directing reflected light radiation from the surface of the wafer; and a second photomultiplier for capturing an image of the reflected light radiation received from the partial reflector; the image of the detected fluorescent energy and the reflected light radiation used to produce a composite image used to evaluate the effectiveness of the wafer drying operation.

25. An apparatus for measuring the effectiveness of a wafer drying operation as recited in claim 24, wherein the source is an Argon laser having a wavelength of about 488 nm.

26. An apparatus for measuring the effectiveness of a wafer drying operation as recited in claim 24, wherein the detected fluorescent energy is created by the source exciting residual molecules of laser dye in the patterned surface of the wafer.

27. An apparatus for measuring the effectiveness of a wafer drying operation as recited in claim 24, wherein the image of the reflected light radiation shows the patterned surface of the wafer.

28. An apparatus for measuring the effectiveness of a wafer drying operation as recited in claim 24, wherein the image of the fluorescent energy shows locations where a selected wafer drying technique did not completely remove a solution from the patterned surface of the wafer.

* * * * *